(12) United States Patent
Janssen et al.

(10) Patent No.: US 11,441,241 B2
(45) Date of Patent: Sep. 13, 2022

(54) ELECTROSPINNING METHOD (71) Applicant: Innovative Mechanical Engineering Technologies B.V, Waalre (NL)

(72) Inventors: Paul Johannes Franciscus Maria Janssen, Eindhoven (NL); Marc Simonet, Eindhoven (NL); Ramon Hubertus Mathijs Solberg, Munstergeleen (NL)

(73) Assignee: Innovative Mechanical Engineering Technologies B.V., Waalre (NL)

( * ) Notice: Subject to any disclaimer, the term of this patent is extended or adjusted under 35 U.S.C. 154(b) by 0 days.

(21) Appl. No.: 16/955,078

(22) PCT Filed: Dec. 18, 2018

(86) PCT No.: PCT/NL2018/050851
§ 371 (c)(1),
(2) Date: Jun. 18, 2020

(87) PCT Pub. No.: WO2019/125148
PCT Pub. Date: Jun. 27, 2019

(65) Prior Publication Data
US 2020/0385889 A1 Dec. 10, 2020

(30) Foreign Application Priority Data
Dec. 19, 2017 (NL) ..................... 2020124

(51) Int. Cl.
*B29C 41/26* (2006.01)
*D01D 7/00* (2006.01)
(Continued)

(52) U.S. Cl.
CPC ......... *D01D 5/0076* (2013.01); *B29C 69/001* (2013.01); *D01D 5/0038* (2013.01);
(Continued)

(58) Field of Classification Search
CPC ............ B29C 2035/0838; B29C 41/26; B29C 69/001; B29C 2791/009;
(Continued)

(56) References Cited

U.S. PATENT DOCUMENTS

2005/0277946 A1* 12/2005 Greenhalgh ....... A61B 17/3421
606/108
2010/0236740 A1* 9/2010 Mourad ................... D04H 1/46
162/289
(Continued)

FOREIGN PATENT DOCUMENTS

CN 106985388 A 7/2017
JP 2015015147 A 1/2015

OTHER PUBLICATIONS

Choi et al, "Structuring Electrospun Polycaprolactone Nanofiber Tissue Scaffolds by Femtosecond Laser Ablation", Journal of Laser Applications, vol. 19, No. 4 (Nov. 2007).*

*Primary Examiner* — Leo B Tentoni
(74) *Attorney, Agent, or Firm* — N.V. Nederlandsch Octrooibureau (57) ABSTRACT

A method of electrospinning (40) is provided, and an electrospinning device (1; 30). The method comprises (i) holding (41) a liquid comprising a polymer melt or a polymer solution in a container (2), (ii) letting out (42) a stream of the liquid from the container through at least one nozzle (3), (iii) creating (43) a voltage difference between the nozzle (3) and a collecting surface (4), (iv) collecting (44) electro spun material coming from the nozzle (3) so as to form a fibrous structure (8) on the collecting surface (4), and (v) directing (45) a laser beam (13) towards the collecting surface (4) so as to locally remove a part of the fibrous structure (8).

9 Claims, 7 Drawing Sheets

(51) Int. Cl.
  *D04H 3/02*   (2006.01)
  *D04H 3/07*   (2012.01)
  *D01D 5/00*   (2006.01)
  *D04H 3/073*  (2012.01)
  *D06M 10/00*  (2006.01)
  *B29C 69/00*  (2006.01)
  *B29C 35/08*  (2006.01)

(52) U.S. Cl.
  CPC ......... *D01D 5/0046* (2013.01); *D01D 5/0092* (2013.01); *D04H 3/073* (2013.01); *D06M 10/005* (2013.01); *B29C 2035/0838* (2013.01); *B29C 2791/009* (2013.01); *B29C 2793/009* (2013.01); *B29C 2793/0045* (2013.01); *D10B 2509/022* (2013.01); *D10B 2509/06* (2013.01)

(58) Field of Classification Search
  CPC ...... B29C 2793/0045; B29C 2793/009; D01D 5/0038; D01D 5/0046; D01D 5/0092; D01D 7/00; D04H 3/02; D04H 3/07; D04H 3/073; D06M 10/005
  USPC ........ 264/154, 171.1, 211.12, 294, 296, 310, 264/400, 465
  See application file for complete search history.

(56) References Cited

U.S. PATENT DOCUMENTS

| | | | |
|---|---|---|---|
| 2012/0000893 A1* | 1/2012 | Broude | B23K 26/032 219/121.69 |
| 2012/0027997 A1* | 2/2012 | Aberg | D21F 1/0036 428/159 |
| 2013/0122248 A1* | 5/2013 | Haselby | D01D 5/0076 264/466 X |
| 2013/0317285 A1 | 11/2013 | Soletti et al. | |
| 2013/0338791 A1* | 12/2013 | McCullen | A61L 27/38 264/466 X |
| 2016/0184058 A1 | 6/2016 | Liu et al. | |
| 2016/0325480 A1 | 11/2016 | Soletti et al. | |
| 2016/0331873 A1 | 11/2016 | Dohse et al. | |

\* cited by examiner

ELECTROSPINNING METHOD

FIELD OF THE INVENTION

The invention relates to an electrospinning device for producing a fibrous structure. The invention also relates to method of electrospinning.

BACKGROUND ART

Electrospinning is a method to produce continuous fibers with a diameter ranging from a few tens of nanometers to a few tens of micrometers. To electrospin fibers, a suitable liquefied material may be fed through a small nozzle. The liquefied material may be electrically charged by applying a high voltage between the nozzle and a counter electrode. The generated electric field causes a cone-shape deformation of the droplet at the nozzle tip. Once the surface tension of this droplet is overcome by the electrical force, a jet is formed out of the droplet and a fiber forms that moves towards the counter electrode. During the flight towards the counter electrode the fiber is continuously stretched and elongated by the different forces acting on it, reducing its diameter and allowing it to solidify by evaporation of the solvent or cooling of the material such that a solid fiber is deposited on the collector which is placed before the counter electrode or the counter electrode is used as collector directly.

Electrospinning uses an electric field, generated by a high voltage potential between nozzle and collector, to produce a fiber from a droplet at the nozzle tip. In alternative configurations fibers are drawn e.g. from a liquid bath, liquid covered ball, liquid filled opening or liquid covered wire.

Electrospun fibrous structures are generally non-woven like, and therefor are, in the plain, generally isotropic in terms of mechanical properties and structure. In order to make an electrospun structure with anisotropic properties, the fibers could be deposited in an aligned structured way. At present, among other methods, such aligned structures can be made using a rotating collector at high rotating speeds. This can be combined for example with a controlled deposition of the fibers. This requires an accurate steering and positioning of the fiber which is very complex up to the point of not even possible.

For application of electrospun structures, among others biological applications, it is not always desirable to have a non-woven or aligned structure at the micro-level in relation to the overall form and performance of the macro structure. This for example in terms directing cell growth and ingrowth, channel and guide fluid flow and creating specific mechanical properties or to minimize overall used and applied material burden while maintaining required functionality.

SUMMARY OF THE INVENTION

It is on object of the present invention to create electrospun fibrous structures with anisotropic mechanical properties or anisotropic structure.

According to a first aspect of the invention, there is provided a method of electrospinning comprising:
(i) holding a liquid comprising a polymer melt or a polymer solution in a container;
(ii) letting out a stream of the liquid from the container through at least one nozzle (3);
(iii) creating a voltage difference between the nozzle and a collecting surface;
(iv) collecting electro spun material coming from the nozzle so as to form a fibrous structure on the collecting surface;
(v) directing a laser beam towards the collecting surface so as to locally remove part of the fibrous structure.

By directing a laser beam towards the collecting surface of an electrospinning device, different parts of the fibrous structure can be targeted without the need for removing the fibrous structure from the collector, which normally leads to an unwanted deformation of the fibrous structure. As a result, predefined parts of the electrospun structure can be removed in a controlled and steered/programmable way. This results in a very accurate patterning in the fibrous structure. By removing predefined parts of the fibrous structure, the structure stiffness and/or transparency can be accurately changed for a multitude of applications.

During the activation of the laser beam, the laser beam may be moved in a pattern or along a path to create the desired design of the hole or cut-out. For example, the laser may be moved so as to create a circular cutout or other closed looped shapes. This enables the removal of relative large parts of the fibrous structure, while only ablating the circumference of the area to be removed.

Optionally, the method further comprises:
(vi) interrupting the laser beam for a moment;
(vii) directing the laser beam towards the collecting surface again so as to locally remove another part of the fibrous structure,
wherein steps (vi) and (vii) are repeated to create a pattern of separated holes or cutouts in the fibrous structure.

By interrupting the laser beam for a moment and directing the laser beam towards another location, the laser beam will produce a number of cutouts or holes. This enables the manufacturing repetitive cutout or holes and as such of more complex patterns in the fibrous structure.

Optionally, the fibrous structure is a layer of fibers. The layer may be 2D or 3D (e.g. tubular). A layer of the fibrous structure can be targeted by a laser beam to create many useful products such as a wound patch (2D) or an artificial trachea (tubular).

Optionally, the laser ablating takes place during the actual electrospinning process. In this way delamination of the various layers is prevented. Delamination may occur when performing the laser processing 'offline'. It is noted that this unwanted delamination of the electrospun fibrous layers can happen already when the electrospinning process is stopped for a very short period of time.

The method in a further embodiment, further comprises the step of rotating the collecting surface (4) by means of one or more rotating bodies.

Optionally after step (vii), the method further comprises the step of adding a fusing layer on top of the patterned fibrous structure.

Optionally, the fibrous structure is tubular shaped and wherein the pattern of separated holes in the fibrous structure are created in such a way that a directional stiffness is created in the tubular fibrous structure.

Optionally, the pattern of separated holes comprises a number of elongated parallel holes each extending in a tangential direction along the circumference of the tubular structure.

Optionally, the elongated parallel holes extend along the circumference of the tubular structure over an angle between 1° and 359°.

Optionally, the laser beam has an energy level wherein the fibrous structure evaporates due to the thermal energy of the laser beam.

The invention also relates to a product manufactured by the method as described above. The product may for example be one of the following:
- a stent;
- an artificial vein;
- an artificial tracheas;
- a wound patch composed of multiple layers.

According to a further aspect there is an electrospinning device comprising:
- a container for holding a liquid comprising a polymer melt or a polymer solution;
- a nozzle arranged to outlet a stream of the liquid from the container;
- a collecting surface;
- a voltage supply system arranged to create a voltage difference between the nozzle and the collecting surface so as to form a fibrous structure on the collecting surface;
- a laser device arranged to direct a laser beam to different locations of the collecting surface,
- a control unit arranged to control the laser beam so as to create separated holes or cutouts in the fibrous structure.

Optionally, the device comprises a rotatable cylindrical body, the surface of which forms a collecting surface for collecting electro spun material coming from the nozzle during an electrospinning process.

Optionally, the control unit is arranged to control the laser beam so as to create a pattern into the fibrous structure.

Optionally, the control unit is arranged to receive a position signal from the rotatable body with its collecting surface as to actively steer the laser to a desired position. Enabling multiple laser processing steps on different layers and contouring of complex shapes.

Optionally, the fibrous structure is tubular shaped and wherein the pattern of separated holes in the fibrous structure are created in such a way that a directional stiffness, is created in the tubular fibrous structure.

SHORT DESCRIPTION OF DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DESCRIPTION OF EMBODIMENTS

Figure 1:
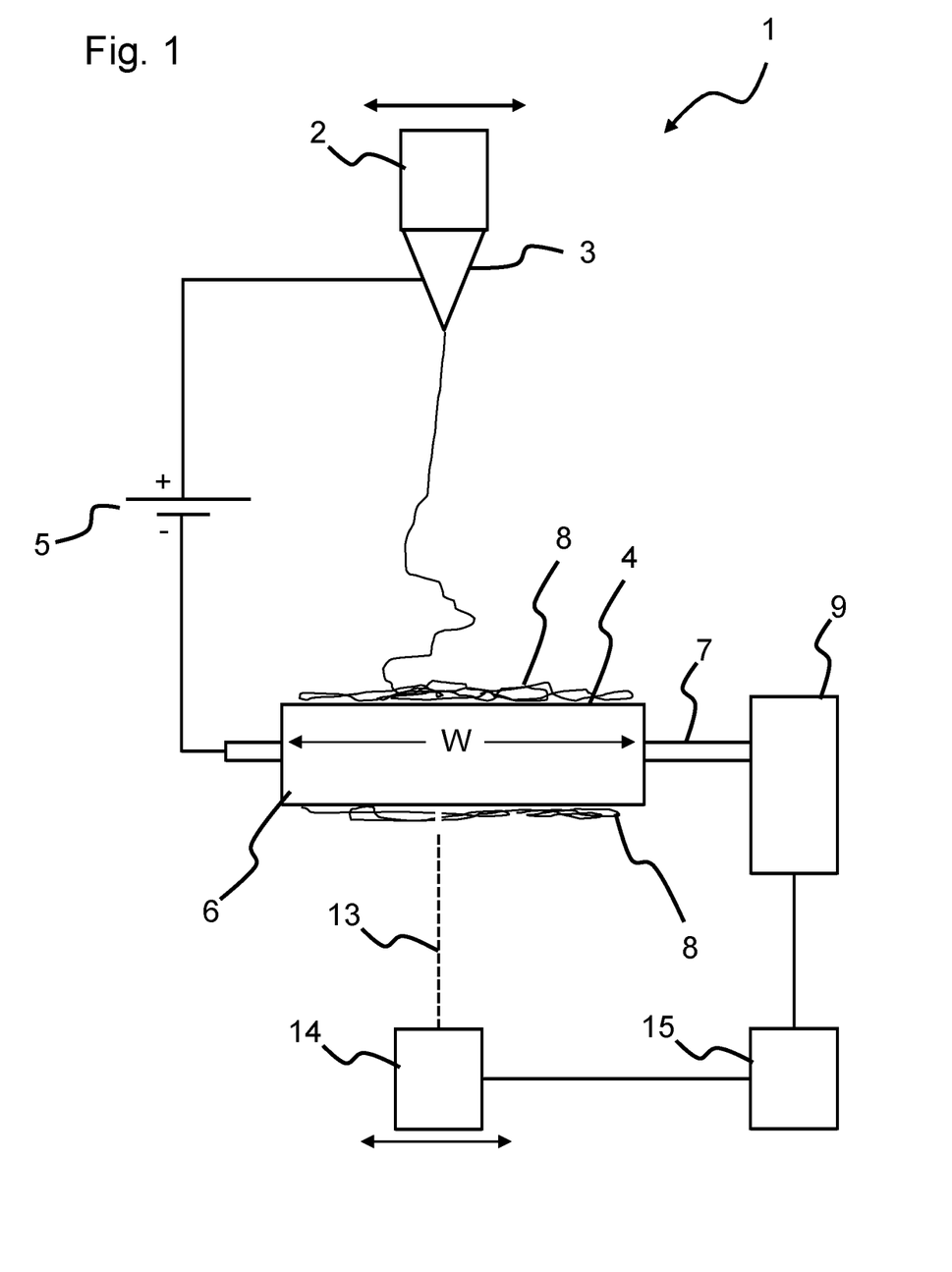
FIG. 1 schematically shows an embodiment of an electrospinning device.

FIG. 1 schematically shows an embodiment of an electrospinning device 1. The electrospinning device 1 may be arranged inside an enclosure (not shown in FIG. 1) for quality or security reasons. The electrospinning device 1 may comprise a container 2 for holding a liquid comprising a polymer melt or a polymer solution, and a nozzle 3 arranged to outlet a stream of the liquid from the container 2. The electrospinning device 1 further comprises a rotating collector 6 with a collecting surface 4 for collecting electro spun material coming from the nozzle 3 during an electrospinning process. A voltage supply system 5 may be arranged to create a voltage difference between the nozzle 3 and the collecting surface 4. The voltage supply system 5 may comprise at least one AC or DC voltage supply to create the voltage difference or it may comprise two voltage supplies, one creating a voltage difference between the collecting surface 4 and ground and one creating a difference between the nozzle 3 and ground. Due to the applied voltage(s), an electro spun fiber is created that flies from the nozzle 3 to the collecting surface 4 on which it is collected to form an electrospun fibrous structure 8. In this embodiment, the collector 6 is arranged onto a shaft 7 which is rotated by means of an actuator 9. Preferably, the nozzle 3 is movable relative to the collector 6 so as to be able to deposit fibers over the whole width W of the collector 6.

A laser device 14 is arranged to direct a laser beam 13 to different locations of the collecting surface 4. The laser device 14 is arranged to produce a laser beam capable of evaporating or ablating electrospun material. A control unit 15 is arranged to control the laser beam 13 so as to create separated holes in the fibrous structure 8. The control unit 15 may be arranged to receive positioning information from the actuator 9 to synchronize the activation of the laser device 14 with the speed and/or orientation of the collecting surface 4.

The laser device 14 may either be placed inside the enclosure, or placed outside with means of guiding the laser beam to inside of the enclosure, directed at the collector of the electrospun fibers. It is noted that laser 'machining' in an offline setup is also possible. In this embodiment, collector and laser beam are arranged movable relative to each other in at least one direction. The laser device 14 may be arranged according to different embodiments:

a) It is movable in a direction parallel to the shaft 7. Preferably, the laser device 14 is movable so as to be able to direct the laser beam 13 over the whole width W of the collector 6, b) The laser source is stationary, laser beam is directed via a moving mirror parallel to the rotational shaft, and/or c) The laser source is stationary, optionally a laser guide, wherein the beam is directed by a galvo scan head.

The control unit 15 may be arranged to control the laser device 14 so as to create a pattern into the fibrous structure 8, as will be explained below.

Figure 2:
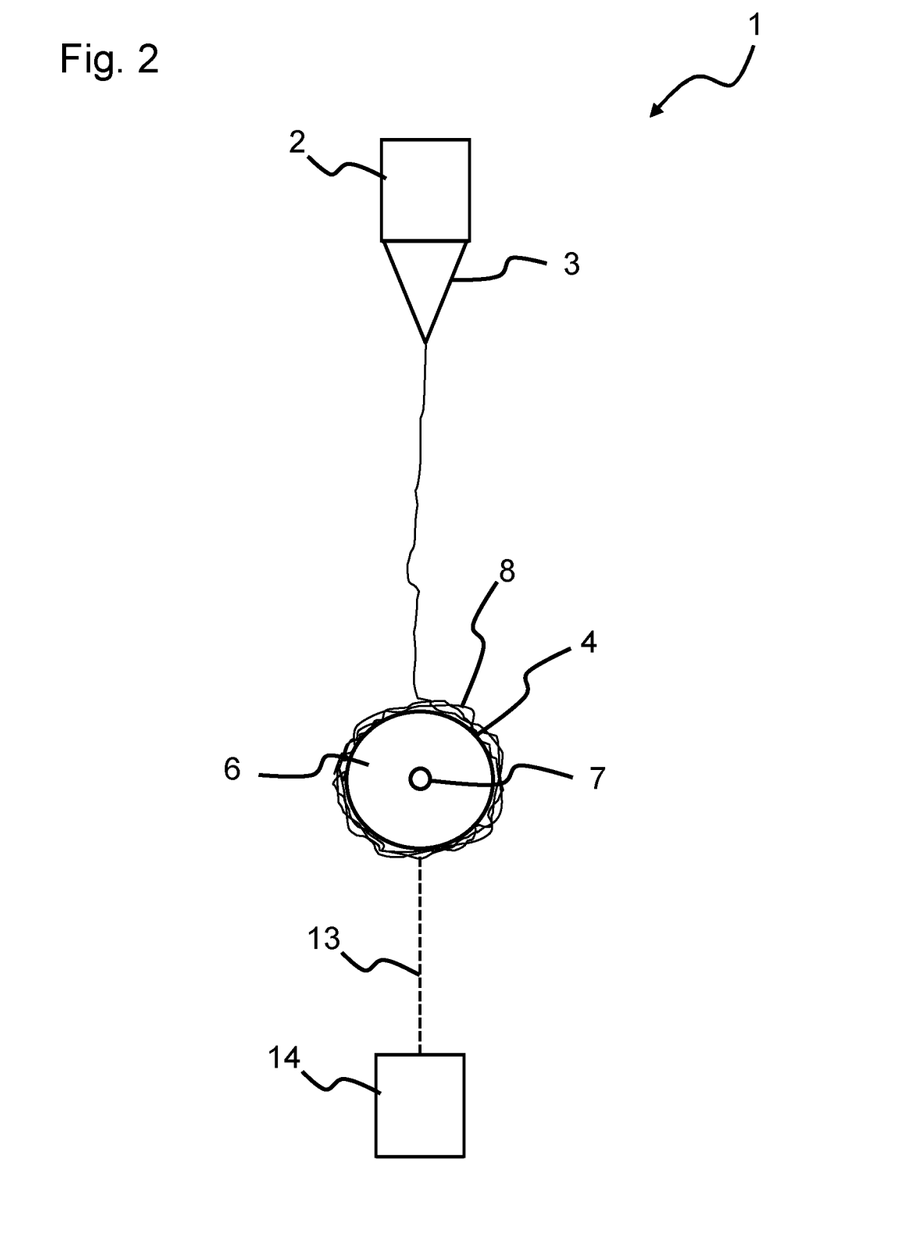
FIG. 2 schematically shows the electrospinning device according FIG. 1 from a different perspective.

FIG. 2 schematically shows the electrospinning device according FIG. 1 from a different perspective. In FIG. 2, the supply system 5, the actuator 9 and the control unit 15 are not shown. As can be seen from FIG. 2, the fibrous structure 8 is collected all around the collecting surface 4, resulting in a layer of fibers. Once removed from the collector 6, the fibrous structure 8 will have a tubular shape, at least from the inside. The outer surface of the fibrous structure 8 may also be tubular shaped, but depending on the amount of fibers collected at a certain area, the outer surface of the structure 8 may have non-cylindrical shapes, for example locally showing a uniform or non-uniform thickness distribution (i.e. heterogeneous distribution).

The electrospinning device may comprise a position measurement system (not shown in FIGS. 1-2) arranged to measure a position of the collector 6 relative to the laser device 14. The measurement system may be arranged to continuously measure the angle of rotation of the collector 6 so as to obtain information on which part of the collector is facing the laser device 14. The control unit 15 may then be arranged to receive position information from the position measurement system and to trigger the laser device 14 in dependency on the received position information. A user may define some locations on the collector at which a hole or cutout is desired. These locations may be programmed in a so-called trigger controller incorporated in the processor of the control unit 15 that triggers the activation of the laser device 14 on the selected programmed positions. Depending on the desired pattern, the laser device 14 is move relative to the collector 6.

Figure 3:
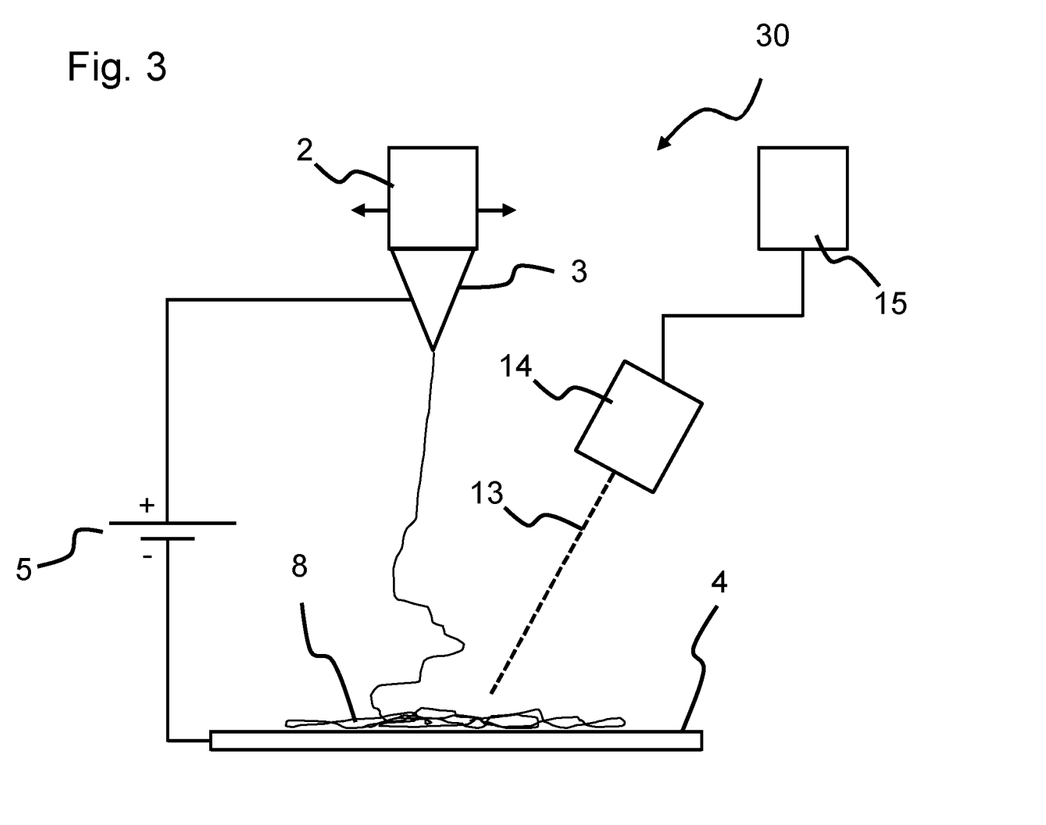
FIG. 3 schematically shows an electrospinning device according to a further embodiment of the invention.

FIG. 3 schematically shows an electrospinning device 30 according to a further embodiment of the invention. In this embodiment, the collecting surface 4 is non-rotating a flat surface extending in two perpendicular directions. The collecting surface 4 may also be curved to some extent or it may have some structure. Similar to the previously described embodiment, a voltage supply system 5 is arranged to create a voltage difference between the nozzle 3 and the collecting surface 4. A laser device 14 is arranged to direct a laser beam 13 onto the collecting surface 4. The laser device 14 is controlled by a control unit 15. The laser device 14 may be movably arranged relative to the collecting surface 4. In this way different parts of the collecting surface 4 can be targeted. It should be noted that in an embodiment, the laser device 14 is arranged to redirect the laser beam 13, so that the collecting surface 4 can be scanned by the laser. This also accounts for the embodiment of FIG. 1. The laser beam 13 may be redirected by means of movable mirrors receiving the laser beam from a laser source. The collecting surface 4 can be stationary as in FIG. 3 or in motion relative to the laser device 14.

Figure 4:
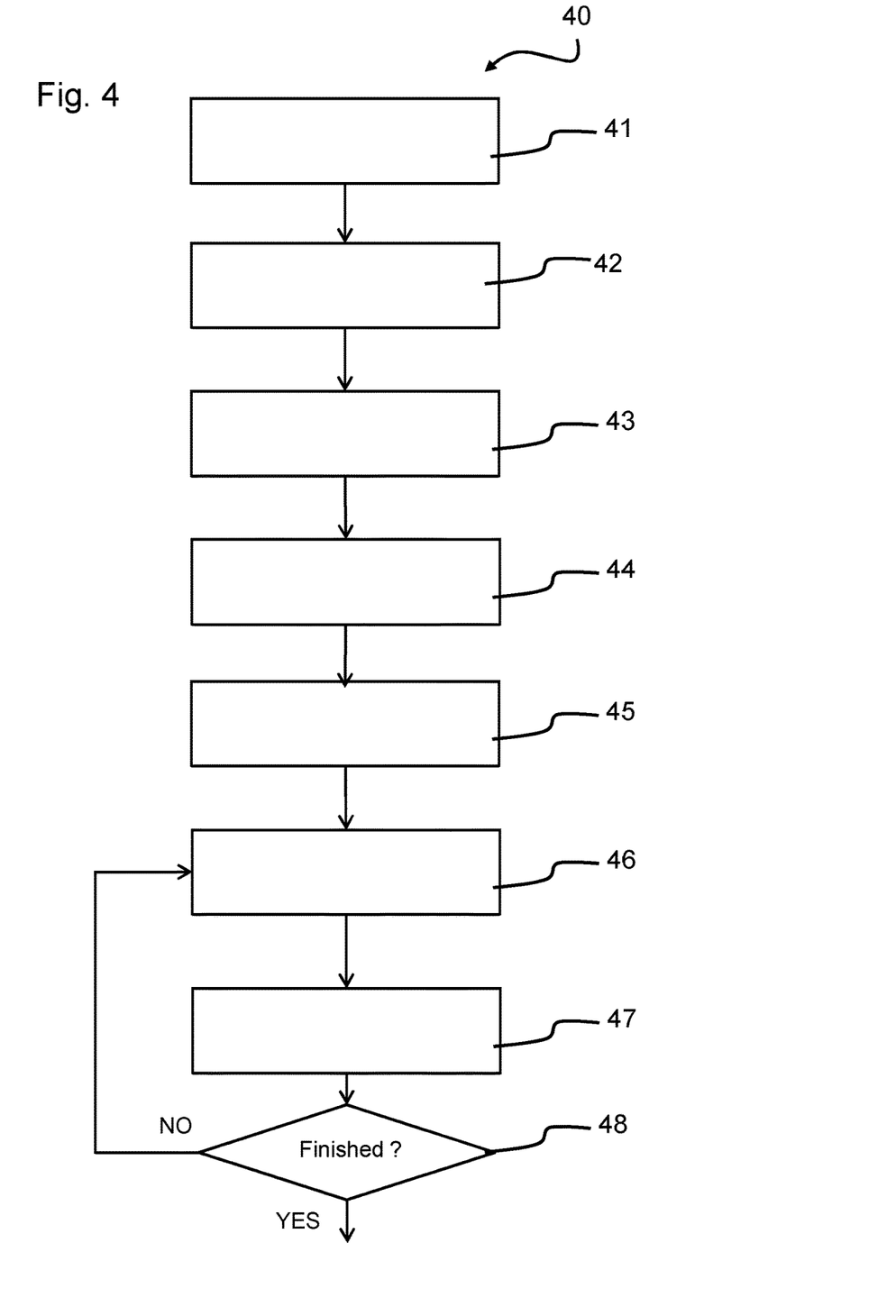
FIG. 4 shows a flow chart of a method of electrospinning according to an aspect of the invention.

FIG. 4 shows a flow chart of a method of electrospinning 40 according to a further aspect of the invention. The method 40 comprises holding, see step 41, a liquid comprising a polymer melt or a polymer solution in a container. Furthermore, the method comprises letting out, see step 42, a stream of the liquid from the container through a nozzle 3. Furthermore the method comprises creating 43 a voltage difference between the nozzle and a collecting surface. Furthermore, the method comprises collecting 44 electro spun material coming from the nozzle so as to form a fibrous structure on the collecting surface. In a next step 45, a laser beam is directed towards a first location on the collecting surface so as to locally remove part of the fibrous structure. Next, the laser beam is interrupted for a moment, see step 46. Then, in a following step 47, the laser beam is directed towards a second location on the collecting surface so as to locally remove another part of the fibrous structure. The steps 46 and 47 are repeated to create a pattern of separated holes in the fibrous structure. The steps 46 and 47 are repeated until the product is finished, as is determined at a test 48.

Figure 5A:
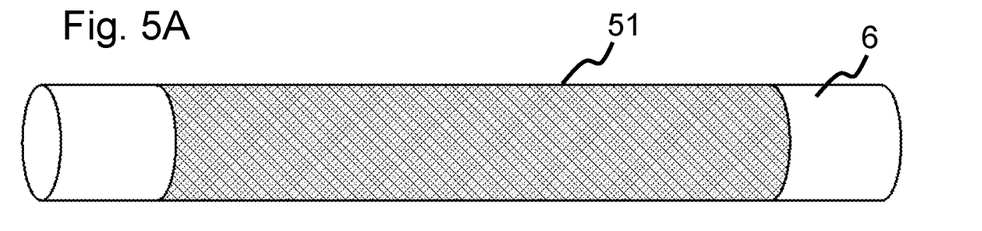
FIGS. 5A-5C show three collectors with fibrous structure during the manufacturing process.
Figure 5B:
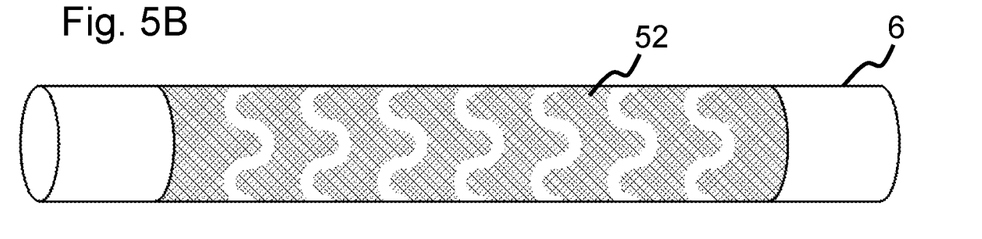
Figure 5C:
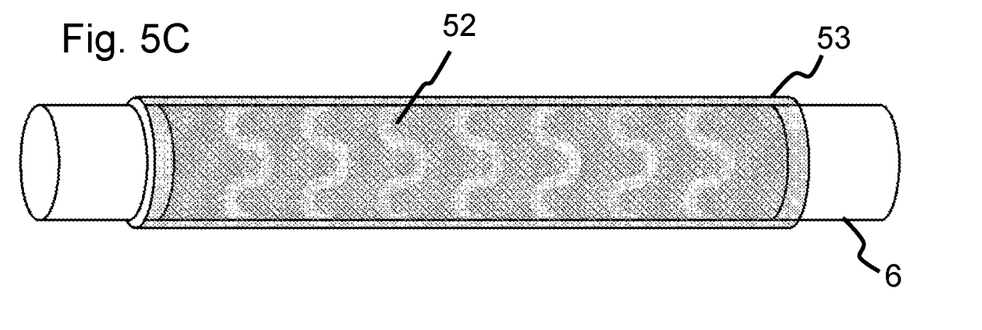

FIGS. 5A-5C show the collector 6 with fibrous structures during consecutive manufacturing steps. FIG. 5A shows the collector 6 after a first electrospun base layer 51 has been spun. Due to the cylindrical outer shape and rotational movement of the collector 6, the base layer 51 has a tubular shape. The thickness and structure, also known as, woven or non-woven of the base layer 51 may be suitably chosen. FIG. 5B shows the same collector 6 as that of FIG. 5A but after a laser beam is used to remove certain parts of the base layer 52. In this way a patterned layer 52 is created. In this example, the laser beam is used to create a number of serpentine patterns along the circumference of the tubular base layer. FIG. 5C shows the same collector 6 and layer 52 as that of FIG. 5B but after a fusing layer 53 has been added. This fusing layer 53 can be created by electrospinning an additional layer on top of the patterned layer 52. Once the electrospun product is removed from the collector 6, it can be used for example as an implantable stent or another type of biological application. Combining a base layer with certain areas removed, and a fusing layer covering the base layer, it is possible to create a product with different mechanical properties as compared to present fiber spun products. For example, a stent can be manufactured having more flexible properties as compared to a simple one layer stent, due to the pattern in the inner layer. A same proposition would hold for a tube. Another application for such or similar pattern could be to introduce a weak line, where the electrospun product could be easily and controlled teared/ripped to a desired size.

Due to the fact that the fusing layer 53 is electrospun using the same material as the base layer, it will adhere to the base layer very easily and a good adhesion can achieved. Even more so if the spinning and ablation is performed simultaneously, hence avoiding the risk of delamination.

It is noted that the invention is not restricted to the manufacturing of multi-layer products. The invention can also be used to manufacture monolayer products or product having another (non-layered) structure, such as product having a 3D configuration.

Figure 6:
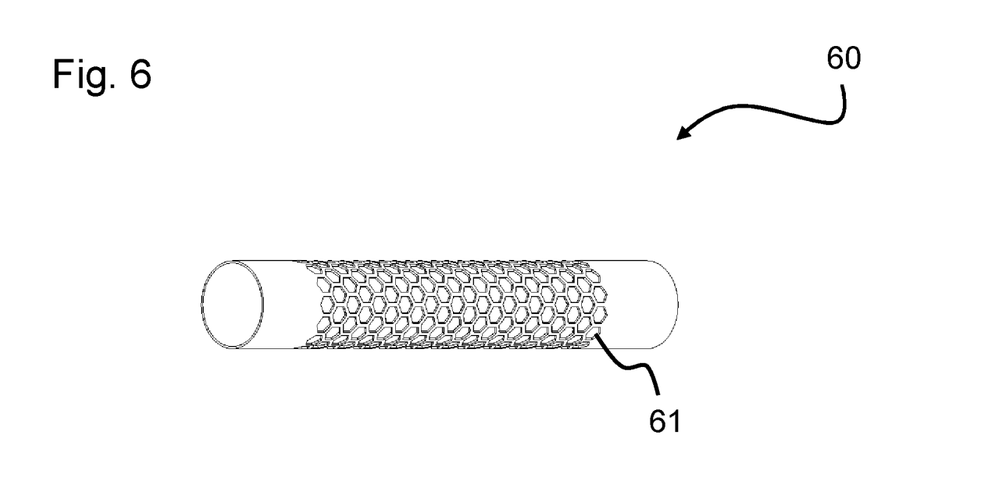
FIG. 6 shows a perspective view of a manufactured product, being a tubular structure having a number of holes in a so-called honeycomb pattern.

FIG. 6 shows a perspective view of a manufactured monolayer product 60, being a tubular structure 60 having a number of holes 61 in a so-called honeycomb pattern. As a result of the holes 61 arranged in a honeycomb pattern, the tubular structure 60 will have a different axial stiffness as compared to a later without the holes 61. So by creating holes in the electrospun structure, the stiffness can be changed in any specific direction.

Instead of changing the stiffness of a structure, the removal of parts of the fibrous structure by the laser may also be used to maximize the mechanical functionality per amount of material. One could reduce the amount of material while maintaining e.g. certain desired mechanical properties of the construct (e.g. stiffness), thereby limiting the amount of material to be implanted in case of a medical implant. As a result, the amount of material that has to be broken down by the body of the patient is reduced, thereby lowering burden for the body.

Figure 7:
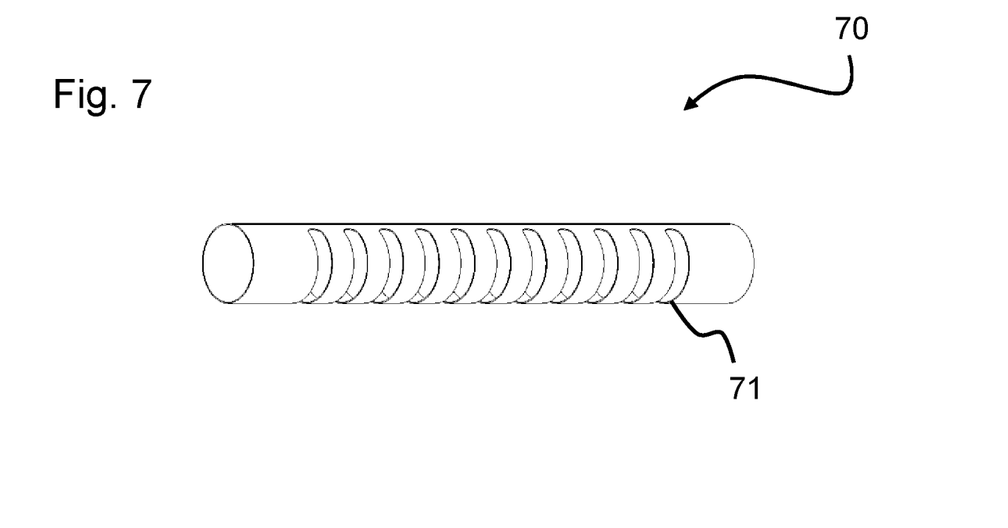
FIG. 7 shows a perspective view of another manufactured product, being a tubular structure having a number of elongated holes.

FIG. 7 shows a perspective view of another manufactured product, being a tubular structure 70 having a number of elongated holes 71. The holes 71 are aligned and are arranged in parallel. Each of the holes 71 extend along the circumference of the tubular structure. The holes do not extend over 360° though. They do not cut the tubular structure in pieces. The pattern shown in FIG. 7 results in a change of stiffness, as compared to a non-layered tubular electro spun structure. The part of the product 70 having the elongated holes will be more flexible in a certain direction, as will be understood by the skilled person. This modified layer can act as a final product or be part of product composed of multiple layers.

Figure 8:
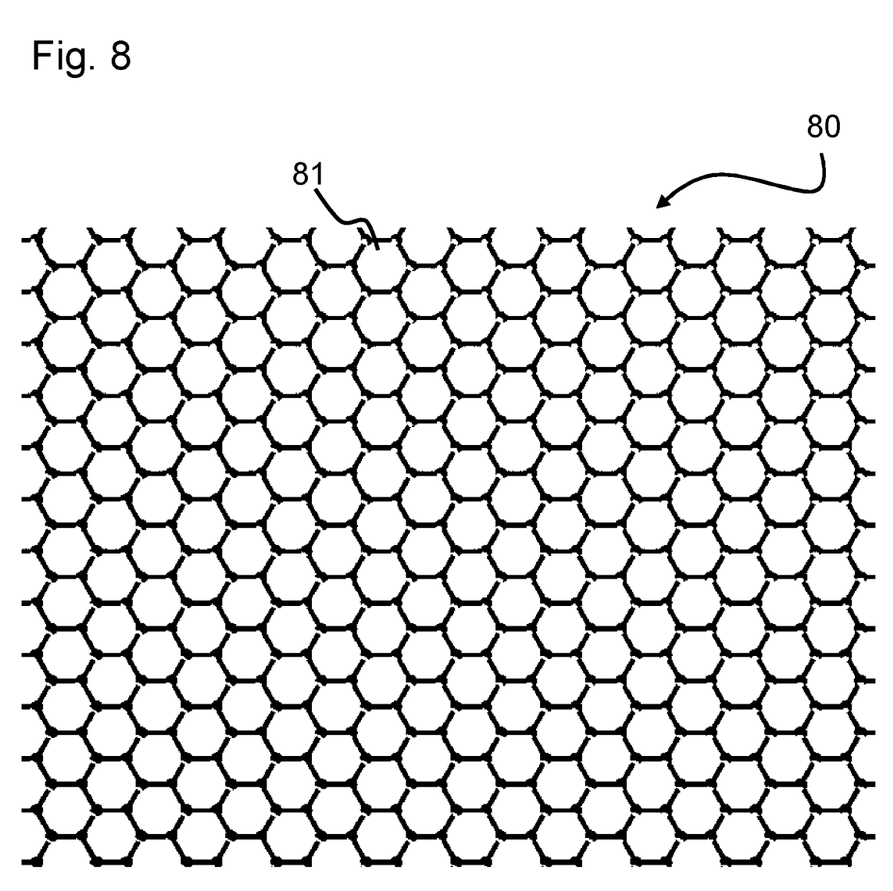
FIG. 8 shows an embodiment of a 2D manufactured product.

FIG. 8 shows an embodiment of a 2D manufactured product 80. The product 80 comprises a lattice of substantially disc-shaped holes 81. The embodiment of FIG. 8 can be used as a wound healing patch, e.g. open drug releasing layer with breathing membrane. This 2D manufactured product 80 can be made using the device 1 shown in FIG. 3. It is noted that the 2D structure could also be made using the embodiment shown in FIG. 1. First a tubular structure can be created, and once finished, the structure can be cut along the length so as to create the 2D product 80.

The present invention enables the making of electrospun structures with tunable/directional mechanical properties of the macro structure. By means of electrospinning deposit a base-layer of fibrous structure on a collector. After the layer has reached a desired thickness (the electrospinning process may continue), a laser is used to remove parts of the structure (by ablation, evaporation or cutting) where flexibility or a different structural feature/imprint is desired. In some cases it might be beneficial to ablate circumference of a large cut-out that has to be removed from the base layer of the structure and subsequently remove the remaining patch instead of having to vaporize the complete patch. If desired the created structure can be fused together again by adding an additional layer of (wet) electrospun fibers. In this way a structure is created with local flexible regions, or regions with reduced amount of material, there where the base-layer is removed, and stiffer parts where the base-layer is intact and covered with the (fusing) layer of fibers. The steps can be repeated and or layers can also be only partially removed/ablated to e.g. create more heterogeneous layers.

The above described method and device will provide more freedom to tailor the macrostructure of electrospun fibrous structure to meet future requirements of stiffness/flexibility so as to create structures with anisotropic mechanical properties or anisotropic structure like for example tracheas, patches with tear lines, construct with induced weak spots aka predetermined breaking points.

It is noted that current techniques do not allow a way of making macro-structures of electrospun fibers with localized flexibility, composed of non-woven, e.g. random oriented or aligned fibers (or a combination of the two), in an accurate, freely programmable and reproducible way. It should be noted that the above-mentioned embodiments illustrate rather than limit the invention, and that those skilled in the art will be able to design many alternative embodiments.

The above mentioned method may also be used to for rotational 3D-lasercutting/modification of cylindrical or free-form scaffolds e.g. heart valve (components), conduits or arteries by means of laser ablation. The laser ablation may be performed in-situ (i.e. without removing from the electrospinning machine), minimizing handling, and enabling automated production.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. In the device claims several means are enumerated. These means may be embodied by one and the same item of hardware or software. The mere fact that certain measures are recited in mutually different dependent claims does not indicate that a combination of these measures cannot be used to advantage.

The invention claimed is:

1. A method of electrospinning comprising:
   (i) holding a liquid comprising a polymer melt or a polymer solution in a container;
   (ii) letting out a stream of the liquid from the container through at least one nozzle;
   (iii) creating a voltage difference between the nozzle and a collecting surface;
   (iv) collecting electro spun material coming from the nozzle so as to form a fibrous structure on the collecting surface;
   (v) directing a laser beam towards the collecting surface so as to locally remove a part of the fibrous structure;
   (vi) interrupting the laser beam for a moment; and
   (vii) directing the laser beam towards the collecting surface again so as to locally remove another part of the fibrous structure,
   wherein steps (vi) and (vii) are repeated to create a pattern of separated holes in the fibrous structure, and
   wherein the pattern of separated holes in the fibrous structure is created in such a way that a directional stiffness is created in the fibrous structure.

2. The method of electrospinning according to claim 1, wherein the fibrous structure is a layer of fibers.

3. The method according to claim 1, wherein the laser beam is directed to the fibrous structure during the collecting of electro spun material on the collecting surface.

4. The method according to claim 1, further comprising the step of rotating the collecting surface by means of one or more rotating bodies.

5. The method according to claim 1, further comprising after step (vii) the step of adding a fusing layer on top of the patterned fibrous structure.

6. The method according to claim 4, wherein the fibrous structure is tubular shaped.

7. The method according to claim 6, wherein the pattern of separated holes comprises a number of elongated parallel holes each extending in a tangential direction along the circumference of the tubular structure.

8. The method according to claim 7, wherein the elongated parallel holes extend along the circumference of the tubular structure over an angle between 1° and 359°.

9. The method according to claim 1, wherein the laser beam has an energy level wherein the fibrous structure evaporates due to the thermal energy of the laser beam.

* * * * *